(12) United States Patent
Takagi

(10) Patent No.: US 6,217,551 B1
(45) Date of Patent: Apr. 17, 2001

(54) INJECTION NEEDLE

(75) Inventor: Hiroshi Takagi, Yokohama (JP)

(73) Assignee: Mitsubishi Pencil Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/500,662

(22) Filed: Feb. 9, 2000

(30) Foreign Application Priority Data

Mar. 3, 1999 (JP) .................................................. 11-054868

(51) Int. Cl.$^7$ ...................................................... A61M 5/00
(52) U.S. Cl. .............................................................. 604/110
(58) Field of Search ...................................... 604/195, 196, 604/197, 198, 110, 187, 192, 218, 220, 225, 226, 263

(56) References Cited

U.S. PATENT DOCUMENTS

| 4,906,236 | * | 3/1990 | Alberts et al. | ........................ 604/198 |
| 5,088,986 | * | 2/1992 | Nusbaum | ............................. 604/195 |
| 5,843,034 | | 12/1998 | Redfern et al. . | |
| 6,056,726 | * | 5/2000 | Isaacson | ................................ 604/164 |

FOREIGN PATENT DOCUMENTS

| 6-142204 | 5/1994 | (JP) . |
| 6-66691 | 9/1994 | (JP) . |
| 7-51372 | 2/1995 | (JP) . |
| 8-141082 | 6/1996 | (JP) . |
| 9-503948 | 4/1997 | (JP) . |
| 9-308690 | 12/1997 | (JP) . |

* cited by examiner

Primary Examiner—Manuel Mendez
(74) Attorney, Agent, or Firm—Darby & Darby

(57) ABSTRACT

In an injection needle provided at the tip of an injector, the injection needle is provided with a properly rotatable operation member in front of a base thereof, an engagement member is fixed rearward on the outer periphery of the needle, a spring is provided in such a manner that the front of the needle is protruded toward the front end of the operation member while the engagement member pierces into the center of an axis of the base and the operation member and the engagement member is energized backward with respect to the base, and the engagement member is latched by the front of the base to hinder the retreat of the engagement member, and when the operation member is rotated with respect to the base from that state, the hindrance to retreat of the engagement member with respect to the base is released, to thereby deeply retreat the needle from the front end of the operation member.

16 Claims, 7 Drawing Sheets

INJECTION NEEDLE

BACKGROUND OF THE INVENTION (1) Field of the Invention

The present invention relates to an injection needle of an injector.

(2) Description of the Prior Art

FIG. 1 is a diagram showing partly in a section an injector A provided with a conventional injection needle.

The conventional injection needle 9 is so formed that a metal needle 11 is fixed by an adhesive or the like on an attachment base 10 made of resin, and the injection needle 9 is fitted to a shaft portion at the front end of a hollow barrel 1 of the injector A.

There is a social problem that the injection needle of the conventional injector may not be properly handled with respect to the safety after use, and erroneously piercing accidents may occur in medical workers, causing an infection from needles contaminated by HIV, HCV and the like. The present invention is to solve such a problem.

SUMMARY OF THE INVENTION

It is an object of the present invention to provide an injection needle which can be easily sealed inside of the injector by a medical worker after use and which can prevent infections by HIV, HCV and the like, due to erroneous piercing of the needle.

The present invention has a construction described below to solve the above problem.

An injection needle according to a first gist of the present invention is an injection needle provided at the tip of an injector, characterized in that the injection needle is provided with a rotatable operation member in front of a base thereof, an engagement member is fixed rearward on the outer periphery of the needle, a spring is provided in such a manner that the front of the needle is protruded toward the front end of the operation member while the engagement member pierces into the center of an axis of the base and the operation member, and the engagement member is energized backward with respect to the base, and the engagement member is latched by the front of the base to hinder the retreat of the engagement member, and when the operation member is rotated with respect to the base from the foregoing state, the hindrance to retreat of the engagement member with respect to the base is released, resulting in a deep retreat of the needle from the front end of the operation member.

An injection needle according to a second gist of the present invention is the injection needle of the first gist, wherein the base can be attached detachably to the shaft portion at the tip of the hollow barrel of the injector.

An injection needle according to a third gist of the present invention is the injection needle of the first gist, wherein the engagement member has a piece portion projecting in the radial direction and extending forward to the front end of a cylinder, and there is provided in the axial center portion of the operation member a manipulation hole to which the piece portion of the engagement member is fitted by insertion to integrate the engagement member with operation member with respect to rotation and there is provided in the axial center portion of a shaft portion in front of the base a retreating hole to which the piece portion is fitted by insertion when the piece portion of the engagement member agrees with the retreating hole, in the state that the front of the needle protrudes from the front end of the operation member, a stepped portion at the rear end of the piece portion of the engagement member is disagreed with the retreating hole and is latched at the front end of the shaft portion in front of the base.

DESCRIPTION OF THE PREFERRED EMBODIMENTS

Figure 1:
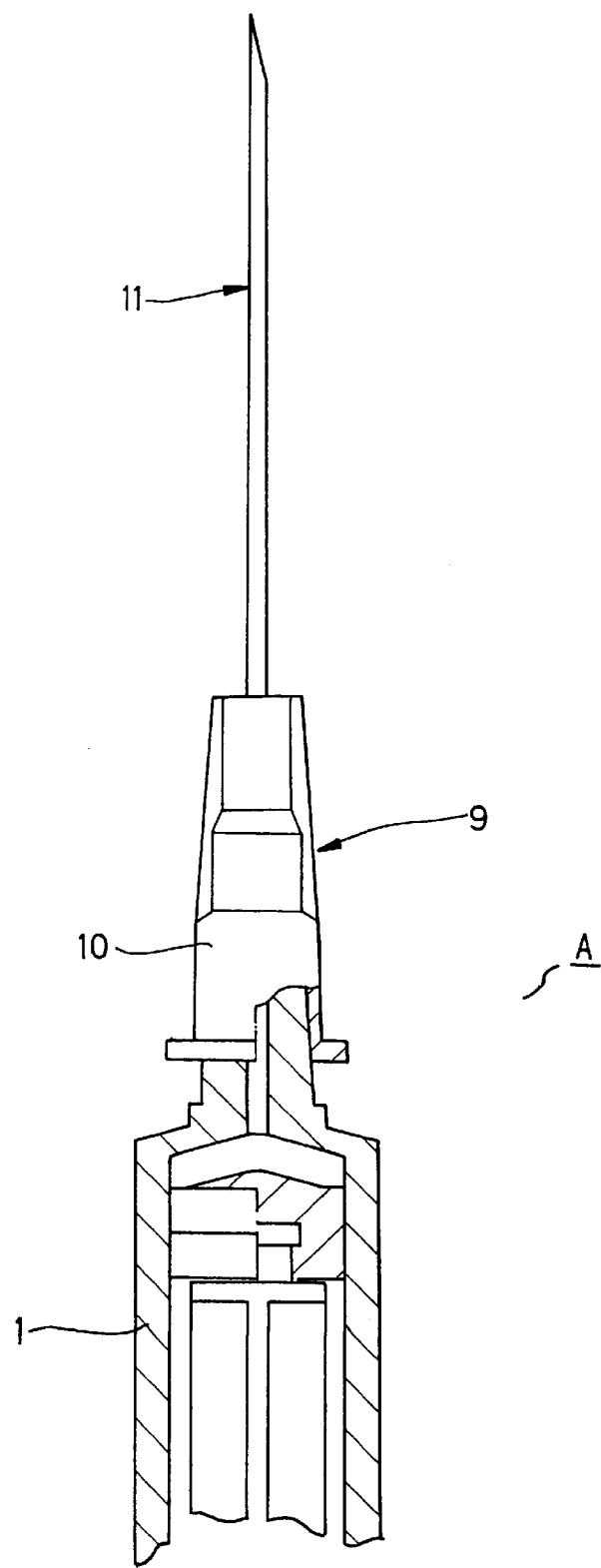
FIG. 1 is a diagram showing a state that a conventional injection needle is attached to an injector.
Figure 2:
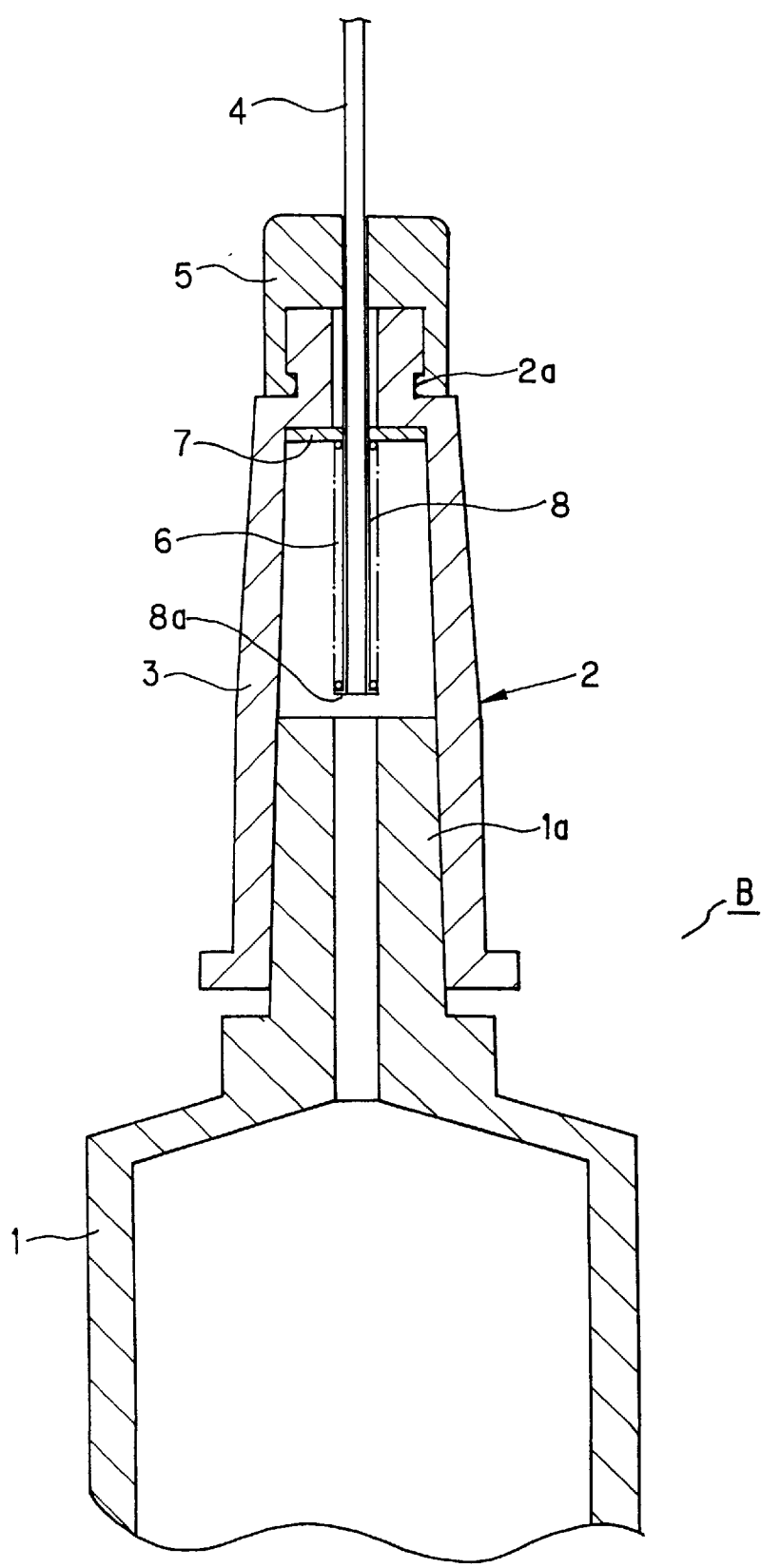
FIG. 2 is a sectional view showing an embodiment of the present invention and shows a state at the time of use of the injector.
Figure 3:
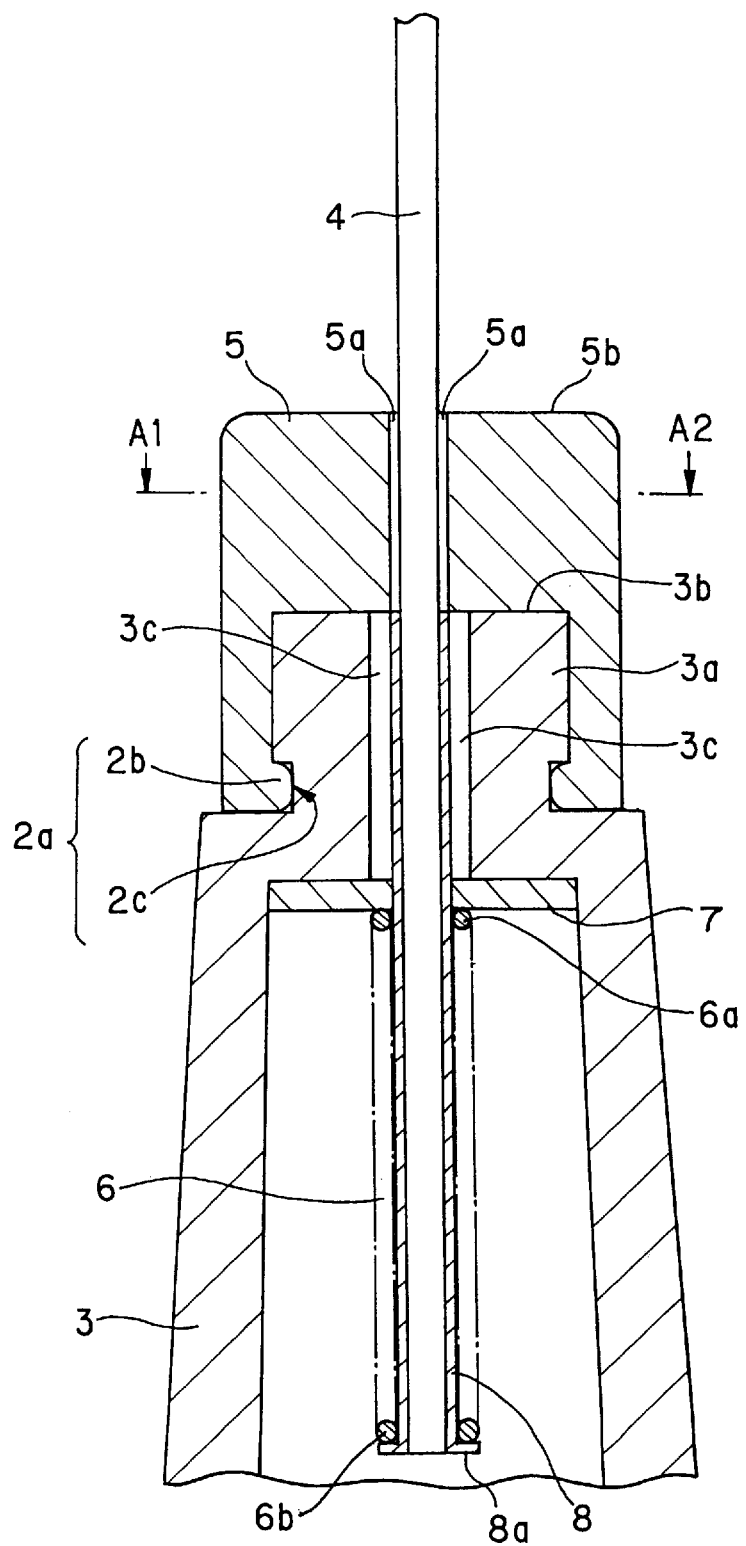
FIG. 3 is an enlarged sectional view showing the main part of FIG. 2.

FIG. 2 and FIG. 3 show an embodiment of the present invention. The same construction is denoted by the same reference numeral.

As shown in the drawings, an injection needle 2 of the present invention is attached to a shaft portion 1a provided at the tip of the hollow barrel 1 of an injector B with the base 3 attached by fitting therewith.

First, the injection needle 2 is constructed by combining a base 3, a needle 4, an operation member 5, a spring 6, a sealing material 7 and an engagement member 8.

Figure 4:
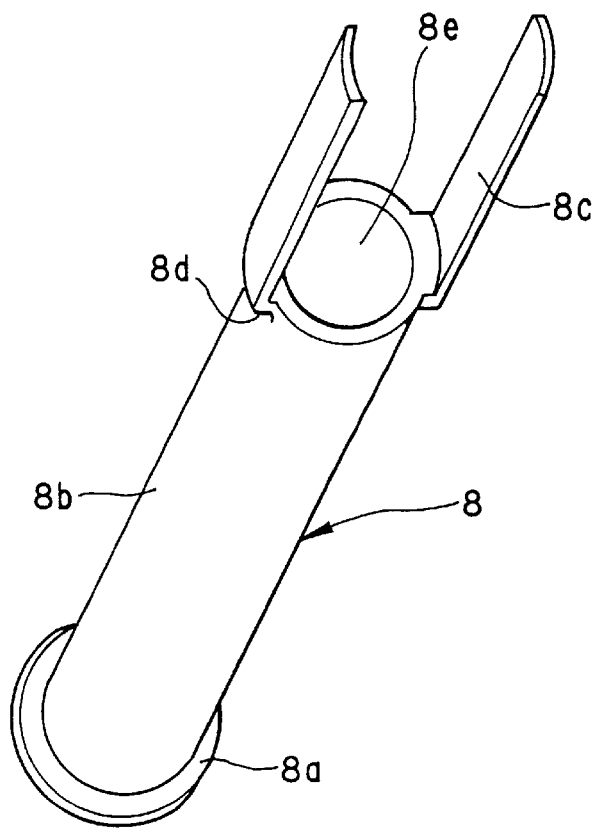
FIG. 4 is a perspective view of an engagement member.

FIG. 4 shows the engagement member 8 which is the gist of the present invention.

The engagement member 8 is provided with a seat portion 8a whose rear end is abutted against the rear end of the spring 6 described later (the seat portion 8a may be attached as a separate member to a sealing material and a spring attachment upper shaft portion 8b), the shaft portion 8b having a hole 8e for fixing the needle 4 described later in the center of the axis, and a piece portion 8c projecting in the radial direction at two positions at the front end of the shaft portion 8b and extending forward, and the rear end of the piece portion 8c becomes a stepped portion 8d. The number of the piece portion 8c is not limited.

Figure 8:
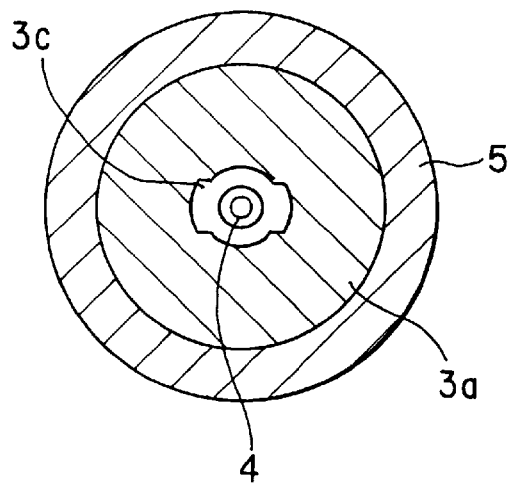
FIG. 8 is a sectional view along the line B1–B2 in FIG. 7.
Figure 9:
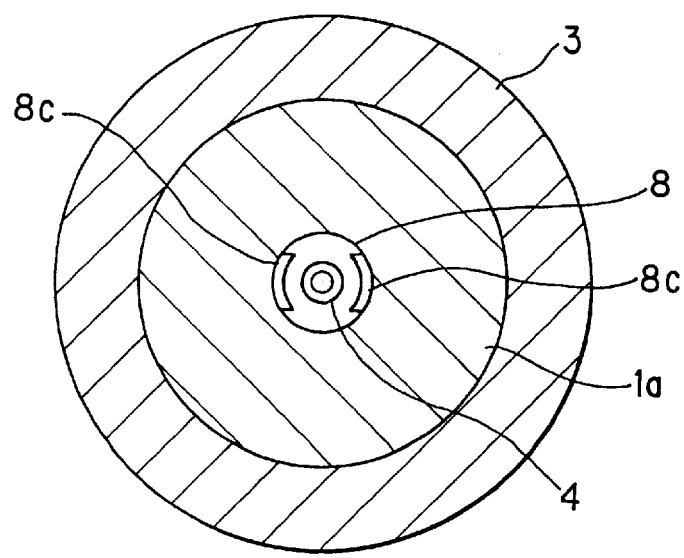
FIG. 9 is a sectional view along the line C1–C2 in FIG. 7.

On the other hand, as shown in FIG. 3, the base 3 has a shaft portion 3a formed in front of a cylinder body thereof, and a concave groove 2c is provided on the outer periphery of the shaft portion 3a. Moreover, in the center of the axis of the shaft portion 3a in front of the base 3 is provided a retreating hole 3c to which the piece portion 8c is fitted together by insertion when the retreating hole 3c coincides with the piece portion 8c of the engagement member 8 on a concentric circle. Therefore, the shape of a cross section of the retreating hole 3c is a circular shape in which a pair of opposing faces are projecting as shown in FIG. 8.

Furthermore, as shown in FIG. 3, the operation member 5 has a protruding portion 2b on the periphery or partly of an inner hole in the rear portion, and in the center of the axis in the front portion is provided a manipulation hole 5a to which the piece portion 8c of the engagement member 8 is fitted by insertion to integrate the engagement member 8 with the operation member 5 with respect to rotation. Therefore, the shape of the cross section of the manipulation hole 5a is a circular shape in which a pair of opposing faces are projecting similar to the retreating hole 3c (see FIG. 5).

In the above described manner, the engagement member 8 is fixed rearward on the outer periphery of the needle 4, the sealing material 7 is passed through the engagement member 8, and the sealing material 7 is abutted against the front end of the inner hole of the base 3 in the state that the front end 6a of the spring 6 is abutted against the rear surface of the sealing material 7 and the rear end 6b of the spring 6 is abutted against the seat portion 8a. The engagement member 8 is pierced out to the retreating hole 3c side via the sealing material 7 in a liquid-tight manner. In the state of FIG. 2 and FIG. 3, the stepped portion 8d provided at the rear end of the piece portion 8c of the engagement member 8 is latched by the end portion 3b of the shaft portion 3a in a disagreed state (normally in a rotation range of about 90).

Figure 5:
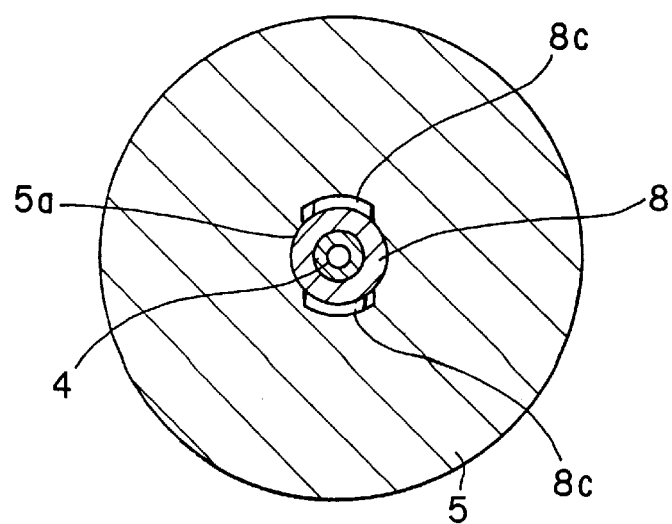
FIG. 5 is a sectional view along the line A1–A2 in FIG. 3.

Next, the operation member 5 is attached so that the piece portion 8c of the engagement member 8 protruding from the end portion 3b of the shaft portion 3a of the base 3 is fitted into the manipulation hole 5a by insertion, and integrated with the engagement member 8 in the direction of rotation (see FIG. 5). The operation member 5 is attached properly rotatably to the base 3 with the protrusion 2b provided in the inner hole at the rear portion being resiliently engaged (engagement portion 2a) with the concave groove 2c provided on the outer periphery of the shaft portion 3a of the base 3. (In addition, the engaging relationship between the above described protrusion 2b and concave groove 2c may be changed.)

Figure 6:
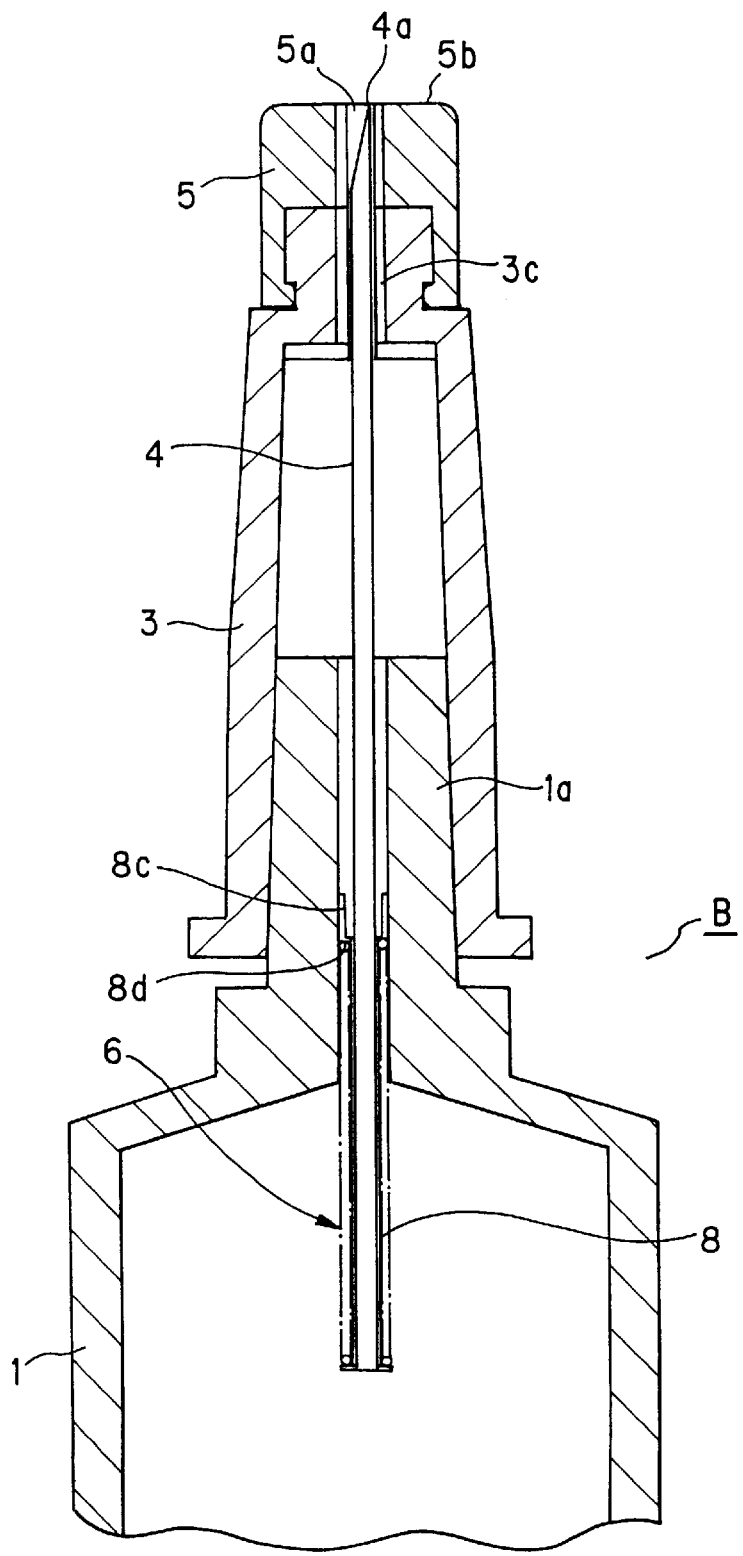
FIG. 6 is a sectional view showing a state after use where the needle is deeply retreated.
Figure 7:
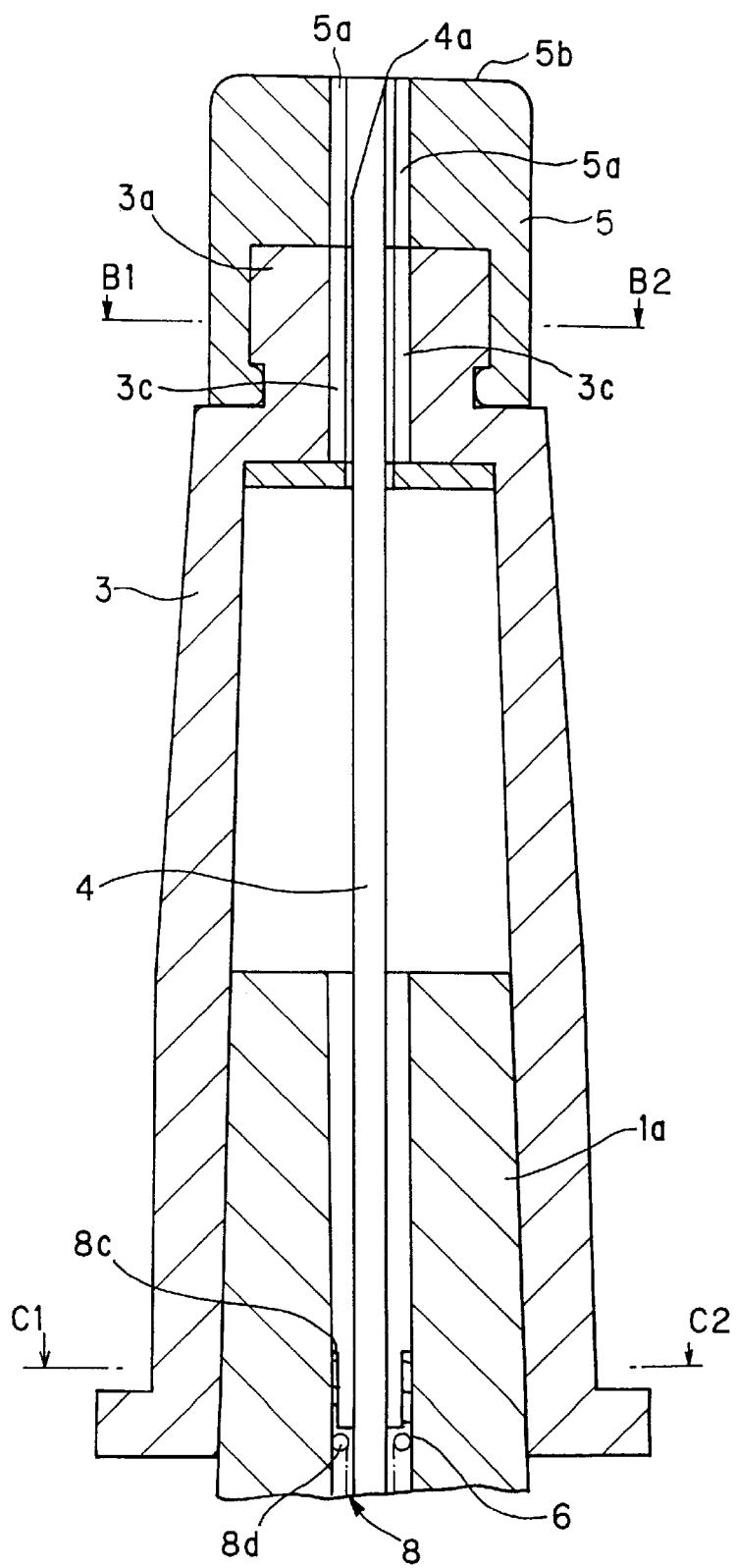
FIG. 7 is an enlarged sectional view showing the main part of FIG. 6.

In this state, the engagement member 8 is latched by the front end portion 3b of the base 3 so that the retreat thereof is hindered, and the front of the needle 4 is protruded from the front end 5b of the operation member 5, thus bringing the service condition of the injector. Moreover, when the operation member 5 (with the engagement member 8) is properly rotated with respect to the base 3 from this state, and the phase of the manipulation hole 5a agrees with the projected portion of the retreating hole 3c, the hindrance of retreat of the engagement member 8 with respect to the base 3 is released, and the tip 4a of the needle is retreated from the front end 5b of the operation member 5 by means of the energizing force of the spring 6 (see FIG. 6 and FIG. 7).

Furthermore, it is desirable to provide means for positioning the rotation range of the operation member 5 with respect to the base 3 in order to latch or release the engagement member 8. The means can be easily realized, therefore the description thereof is omitted.

As described above, the present invention relates to the safety of the injector, and the injector can be used by putting the engagement member 8 fixed to the needle 4 into the latched state, and by properly rotating the operation member 5, the engaged state is released to thereby deeply retreat the needle 4 backward of the operation member 5 by means of the force of the spring 6.

Conventionally there is a social problem in that the injection needle may not be properly handled after use, and erroneously piercing accidents may occur in medical workers, causing an infection from needles contaminated by HIV, HCV and the like. With the present invention, however, the needle after use can be immediately turned into a state that the needle is not exposed, enabling to solve the conventional problem.

What is claimed is:

1. An injection needle provided at the tip of an injector, wherein the injection needle is provided with a rotatable operation member in front of a base, an engagement member is fixed rearward on an outer periphery of the needle, a spring is provided in such a manner that a front of the needle extends from a front end of the operation member while the engagement member pierces into a center of an axis of the base and the operation member, and the engagement member is energized backward with respect to the base, and the engagement member is latched by a front of the base to hinder the retreat of the engagement member, and when the operation member is rotated with respect to the base from the foregoing state, the hindrance to retreat of the engagement member with respect to the base is released, resulting in a deep retreat of the needle from the front end of the operation member.

2. An injection needle according to claim 1, wherein the base can be attached detachably to a shaft portion at a tip of a hollow barrel of the injector.

3. An injection needle according to claim 1, wherein the engagement member has a piece portion projecting in a radial direction and extending forward to a front end of a cylinder, and there is provided in an axial center portion of the operation member a manipulation hole to which the piece portion of the engagement member is fitted by insertion to integrate the engagement member with operation member with respect to rotation and there is provided in the axial center portion of a shaft portion in front of the base a retreating hole to which the piece portion is fitted by insertion when the piece portion of the engagement member agrees with the retreating hole, in the state that the front of the needle protrudes from the front end of the operation member, a stepped portion at the rear end of the piece portion of the engagement member is disagreed with the retreating hole and is latched at the front end of the shaft portion in front of the base.

4. An injection needle assembly including an injection needle provided at a tip of an injector, the injection needle assembly comprising:

a base for connection to the injector, the base having an opening formed therethrough for receiving the needle;

a rotatable operation member rotatably attached to a front end of the base, the operation member having an opening formed therethrough for receiving the needle; and an engagement member attached to an outer periphery of the needle; the engagement member being positionable in first and second positions, wherein in the first position, the engagement member is spring biased rearwardly with respect to the base such that a front section of the needle protrudes through the openings of the base and operation member and extends from a front end of the operation member, while the engagement member is latched to the base so that the needle is prevented from retreating within the base, and wherein rotation of the operation member causes the openings of the base and operation member to align with one another resulting in the engagement member being disengaged from the base and an energizing force of the spring causes the needle to deeply retreat within the base from the front end of the operation member.

5. The assembly of claim 4, wherein the engagement member includes an elongated shaft portion having an opening formed therethrough to receive the needle, the engagement member having a portion projecting in the radial direction from a front end of the shaft portion of the engagement member.

6. The assembly of claim 5, wherein the projecting portion comprises a pair of opposing portions which project in a radial direction at two locations at the front end of the shaft portion.

7. The assembly of claim 5, wherein the projecting portion extends from the front end of shaft portion and a rear end of the projecting portion forms a stepped portion at the front end of the shaft portion.

8. The assembly of claim 7, wherein the engagement member includes a seat portion formed at a rear end of the shaft portion, the spring being disposed between the stepped portion and the seat portion in the second position.

9. The assembly of claim 7, wherein the engagement member is latched to the base by an interference fit between the stepped portion and the front end of the base.

10. The assembly of claim 9, wherein the interference fit is removed when the operation member is rotated and the openings of the operation member and the base align with one another.

11. The assembly of claim 9, wherein a cross section of the opening of the base is generally circular in shape with a pair of opposing first faces being formed to complementarily receive the stepped portion of the engagement member.

12. The assembly of claim 11, wherein a cross section of the opening of the operation member complements the opening of the base in that it is generally circular in shape with a pair of opposing second faces being formed, the engagement member being coupled to the operation member by inserting the projecting portion in the opposing second faces.

13. The assembly of claim 11, wherein the interference fit is removed when the projecting portion is fitted by insertion into the opening formed in the base when the stepped portion aligns with the opposing first faces.

14. The assembly of claim 11, wherein the interference fit is formed when the projecting portion of the engagement member is axially offset from opposing first faces of the opening formed in the base.

15. The assembly of claim 4, wherein the operation member includes a protruding portion which engages a groove formed in the base so as to rotatably couple the operation member to the base.

16. The assembly of claim 4, wherein the opening formed in the base includes a reduced section formed at the front end of the base, the assembly having a sealing material disposed within the base in an abutting manner relative to the reduced section of the opening, a front end of the spring abutting against a rear surface of the sealing material in the first position, the engagement member piercing the seal material in a liquid-tight manner.

* * * * *